United States Patent [19]

Kwantes et al.

[11] 4,045,379

[45] Aug. 30, 1977

[54] PROCESS FOR PREPARATION OF MODIFIED ION-EXCHANGE RESIN

[75] Inventors: Ariën Kwantes; Pieter A. Gautier; Anthony L. Farragher, all of Amsterdam, Netherlands

[73] Assignee: Shell Oil Company, Houston, Tex.

[21] Appl. No.: 708,522

[22] Filed: July 26, 1976

[30] Foreign Application Priority Data

Aug. 1, 1975 United Kingdom .............. 32251/75

[51] Int. Cl.$^2$ .......................... C08F 8/34; C07C 37/00
[52] U.S. Cl. ....................... 260/2.2 R; 260/79.5 NV; 260/619 A
[58] Field of Search ........... 260/619 R, 619 B, 619 H, 260/2.1 R, 2.2 R, 79.5 NV

[56] References Cited

U.S. PATENT DOCUMENTS

| 3,634,341 | 1/1972 | Gammill et al. | 260/619 A |
| 3,760,006 | 9/1973 | Gammill et al. | 260/619 A |

Primary Examiner—Joseph L. Schofer
Assistant Examiner—Peter F. Kulkosky

[57] ABSTRACT

An improved process for preparing bisphenols is described wherein a phenol is reacted with a ketone or aldehyde such as acetone in the presence of an ion-exchange resin modified by partial neutralization with p-aminothiophenol.

2 Claims, No Drawings

PROCESS FOR PREPARATION OF MODIFIED ION-EXCHANGE RESIN

BACKGROUND OF THE INVENTION

It is known to prepare bisphenols by reacting a phenol with a carbonyl compound in the presence of a substantially water-insoluble cation-exchange resin containing sulfonic acid groups. See, for example, British Pat. No. 849,965. It is also known to use modified resin catalysts in the above process. Modification may be carried out by either partially esterifying the resin with a mercapto alcohol as described in British Pat. No. 937,072, or by partially neutralizing the resin with an alkyl mercaptoamine as described in British Pat. No. 1,183,564.

A new class of modified resin catalysts has now been discovered which is useful in the above process. This new class of resin catalysts contains a plurality of sulfonic acid groups and a plurality of cyclic mercaptoamine sulfonic acid salt groups.

SUMMARY OF THE INVENTION

The invention relates to a novel resin catalyst, to a process for the preparation of bisphenols, and to the bisphenols so prepared.

According to one aspect of the invention, a catalyst, suitable for catalyzing the reaction between a phenol and a carbonyl compound, comprises a substantially water-insoluble cation-exchange resin containing a plurality of sulfonic acid groups and a plurality of mercaptoamine sulfonic acid salt groups, characterized in that the salt groups are cyclic mercaptoamine sulfonic acid salt groups.

According to another aspect of the invention, a process for the preparation of bisphenols comprises reacting a phenol with a carbonyl compound in the presence of a water-insoluble cation-exchange resin containing a plurality of sulfonic acid groups and a plurality of cyclic mercaptoamine sulfonic acid salt groups.

DESCRIPTION OF THE PREFERRED EMBODIMENTS

The cyclic mercaptoamines, i.e., compounds which contain at least one ring structure, at least one mercapto group and at least one amino group, which is preferably a primary amino group, from which the modified resin catalysts are prepared, are suitably compounds in which the mercapto and amino groups are both directly attached to the ring structure. Preferred compounds are aromatic mercaptoamine i.e., compounds containing an aromatic nucleus, a mercapto group and an amino group. Most preferred aromatic mercaptoamines are those in which both the mercapto and the amino groups are directly bound to the aromatic nucleus. Preferably the amino and mercapto groups are attached to ring carbon atoms which are separated from each other by at least one ring carbon atom. A particularly preferred aromatic mercaptoamine is 1,4-aminothiophenol which may be optionally substituted by one or more lower alkyl groups, e.g. by one or more alkyl groups of from 1 to 4 carbon atoms.

The modified resin catalyst may be prepared from any cation-exchange resin containing a plurality of sulfonic acid groups. The structure of the resin should be such so as to render the modified resin catalyst insoluble in the reaction mixture. The exchange capacity of the sulfonated resin, used to prepare the modified resin catalyst, is preferably at least 2.0 meq/g dry weight, with exchange capacities in the range of from 3.0 to 5.5 meq/g dry weight being particularly preferred. Suitable resins may be of the gel or macroreticular type. Examples of suitable resins are sulfonated styrene-divinylbenzene copolymers, sulfonated phenol-formaldehyde resins and sulfonated benzene-formaldehyde resins. The sulfonated resin is suitably in the acid form. Sulfonated resins are commercially available in a dry or water-swollen form and either form may be used to prepare the modified resin catalyst. Specific examples of suitable resins are Amberlite IR-120H, Amberlite XE 307, Amberlyst 15H, Dowex 50-X-4, Dowex MSC-1H, Duolite C-20, Permutit QH, and Chempro C-20. (Amberlite, Amberlyst, Dowex, Duolite, Permutit and Chempro are registered Trade Marks).

The modified resin catalyst may be prepared by several techniques but preferred techniques are those which result in the cyclic mercaptoamine salt groups being substantially equally distrubuted over the resin. One technique is to partially neutralize the whole of the sulfonated resin with the cyclic mercaptoamine or a salt thereof. This may be easily achieved by adding the cyclic mercaptoamine or a salt thereof, in a predetermined amount, to an aqueous slurry of the sulfonated resin. Other techniques include fully neutralizing a portion of the sulfonated resin and intimately mixing this fully neutralized resin with unneutralized sulfonated resin, preferably in the form of water-swollen sulfonated resin.

It is preferred that from 2 to 25%, particularly from 5 to 15%, of the sulfonic acid groups of the sulfonated resin are neutralized to form cyclic mercaptoamine sulfonic acid salt groups. This degree of neutralization corresponds to a modified resin catalyst containing from 3 to 49, more preferably from about 6 to 19, sulfonic acid groups for each salt group present therein. Preferably the exchange capacity of the modified resin catalyst is from about 2.6 to about 5.2 meq/g dry weight.

The modified resin catalyst prepared as above may be dehydrated before it is used in the process, e.g., by oven-drying, azeotropic distillation with phenol or toluene or by treatment with liquid phenol. Alternatively the modified resin catalyst may, when being used in a fixed bed continuous reactor, be dehydrated by pretreating the resin bed with anhydrous phenol. However, it is not necessary to dehydrate the catalyst before use or to pre-treat the resin bed since the general reaction conditions especially when initially high flow rates of reactants are used, will rapidly remove water from the modified resin catalyst.

The modified resin catalyst as described above may be used to prepare many bisphenols. The phenols used in the process should have a reactive hydrogen atom, preferably in the para-position relative to the phenolic hydroxyl group. Such phenols may be substituted by one or more alkyl groups, e.g. lower alkyl groups such as methyl or tertiary butyl groups, halogen atoms, such as chlorine atoms, or other non-interfering substituents. Specific examples of phenols include ortho- and meta-cresol; 2,6-dimethylphenol; ortho-sec.butyl phenol; ortho-tert.butylphenol; 2,6-di-tert.butylphenol' 1,3,5-xylenol; tetramethylphenol; 2-methyl-6-tert.butylphenol; ortho-phenylphenol; ortho- and meta-chlorophenol; ortho-bromophenol; 6-chloro-ortho-cresol and 2,6-dichlorophenol. Phenol itself is the preferred phenol.

The carbonyl compounds used in the process may be aldehydes or ketones with the latter being preferred. Preferred ketones are those having at least one methyl group alpha to the carbonyl group or are cyclic ketones. Specific examples include acetone, methyl ethyl ketone, methyl propyl ketone, acetophenone, methyl vinyl ketone and cyclohexanone. Acetone is the preferred ketone.

The molar ratio of phenol to carbonyl compound is suitably at least 2:1 with a molar excess of phenol being preferred. Suitable molar ratios are from 3:1 to 25:1, with molar ratios of from 6:1 to 20:1 being preferred. The optimum ratio depends inter alia on reaction conditions, e.g. temperature of reaction; desired conversion and whether or not a batch or continuous process is used.

The reaction temperature may vary between wide limits with a reaction temperature in the range of from 30° C to 120° C being suitable and a reaction temperature in the range of from 40PC to 100° C being preferred.

The reaction time may also vary between limits and depends inter alia on reaction temperature and whether or not a batch or continuous process is used. For example, in a continuous process using a fixed catalyst bed an average contact time of from 5 minutes to 5 hours may be used.

The bisphenol may be recovered from the product mixture by conventional techniques e.g. by removing the acetone, phenol, water and by-products by flash distillation. The residual bisphenol may also be purified by conventional techniques e.g. distillation, crystallization. solvent washing and similar techniques.

The bisphenols prepared by the present invention may be used in a variety of applications such as to prepare anti-oxidants, epoxy resins and polycarbonate resins.

The following embodiments illustrate the preparation of the instant modified catalyst and the prepation of bisphenol A from this novel catalyst, and are for the purpose of illustration only and are in no way intended to limit the invention to the particular compositions illustrated. Modifications within the spirit and scope of the present invention will become apparent to those skilled in the art. Parts and percentages are by weight unless otherwise noted.

ILLUSTRATIVE EXAMPLE I

This example illustrates the preparation of the aminothiophenol-modified ion-exchange resin.

An aqueous slurry was prepared contaning 15 pbw (dry basis) of a macroreticular styrene-divinylbenzene strong acid cation-exchange resin having an exchange capacity of 4.84 meq/g dry weight. The slurry was heated to 60° C; 0.9 g of 1,4-aminothiophenol added and the mixture gently stirred for 30 minutes.

The modified resin so prepared had an exchange capacity of 4.36 meq/g dry weight which corresponds to about 10% neutralization of the initial acidity of the resin.

ILLUSTRATIVE EXAMPLE II

This example illustrates the preparation of bisphenol A using the modified catalyst from Example I.

A reactor tube (25 ml) was filled with the slurry of modified resin catalyst as prepared in Example I and excess water drained off resulting in a tube filled with 25 ml of water-swollen catalyst containing about 50% w of water.

The reactor tube was heated to, and maintained at, a temperature of about 65° C by means of circulating hot oil. A feedstock solution of acetone in molten phenol (molar ratio of phenol to acetone of about 15:1) was fed to the reactor at a rate of about 50 ml/hour (LHSC of 2 liters feed/liter reactor/hour). The reactor effluent, a water-white liquid, was analyzed for acetone content.

The acetone conversion after 6 run hours, calculated on the basis of feedstock and effluent composition was 58%. The composition of the product produced was 4.5% ortho/para bisphenol A, 95.5% para/para bisphenol A. A product contained 0.05%, on bisphenol A, of Dianin's compound.

The acetone conversion and the composition of the bisphenol A after 50 run hours was the same as the above.

What is claimed is:

1. A substantially water-insoluble cation exchange resin having an exchange capacity of from 2.6 to 5.2 meq/g dry weight comprising a plurality of mercaptoamine sulfonic acid salt groups, wherein said salt groups are cyclic aromatic mercaptoamine sulfonic acid salt groups wherein the mercapto and the amino groups are bound directly to the aromatic nucleus thereof.

2. The resin of claim 1 wherein the aromatic mercaptoamine is 1,4-aminothiophenol.